United States Patent

Hartman et al.

[11] Patent Number: 6,146,369
[45] Date of Patent: Nov. 14, 2000

[54] MECHANICAL CLOSURE WITH SLIT CARRIER FOR DISPOSABLE DIAPERS

[75] Inventors: William G. Hartman, North Royalton; Michael D. Hilston, Painesville, both of Ohio

[73] Assignee: Avery Dennison Corporation, Pasadena, Calif.

[21] Appl. No.: 09/101,565

[22] PCT Filed: Jan. 16, 1997

[86] PCT No.: PCT/US97/00616

§ 371 Date: Oct. 9, 1998

§ 102(e) Date: Oct. 9, 1998

[87] PCT Pub. No.: WO97/25953

PCT Pub. Date: Jul. 24, 1997

Related U.S. Application Data

[60] Provisional application No. 60/010,075, Jan. 16, 1996.

[51] Int. Cl.[7] ................................................ A61F 13/15
[52] U.S. Cl. ............................ 604/391; 604/386; 24/442
[58] Field of Search .................................... 604/386, 391, 604/385.01; 24/306, 442, 446, 550

[56] References Cited

U.S. PATENT DOCUMENTS

| | | | |
|---|---|---|---|
| 3,932,328 | 1/1976 | Korpman | 260/27 BB |
| 4,787,897 | 11/1988 | Torimae et al. | |
| 4,795,456 | 1/1989 | Borgers et al. | 604/390 |
| 4,834,820 | 5/1989 | Kondo et al. | 156/73.3 |
| 4,869,724 | 9/1989 | Scripps | 604/389 |
| 5,019,065 | 5/1991 | Scripps | 604/385.1 |
| 5,053,028 | 10/1991 | Zoia et al. | 604/385.1 |
| 5,318,555 | 6/1994 | Siebers et al. | |
| 5,605,735 | 2/1997 | Zehner et al. | |
| 5,795,350 | 8/1998 | Schmitz | 604/391 |
| 5,916,207 | 6/1999 | Toyoda et al. | 604/391 |

*Primary Examiner*—Mark O. Polutta
*Attorney, Agent, or Firm*—Pearne & Gordon LLP

[57] ABSTRACT

An extensible tab fastener for a disposable diaper comprises a laminate of an extensible facestock and an ordinarily nonextensible mechanical fastener. The nonextensible mechanical fastener is rendered extensible by providing in at least the nonextensible portions thereof a plurality of separation interfaces or parting planes extending through the thickness of the nonextensible portion or portions at spaced locations in the direction of desired extensibility.

9 Claims, 1 Drawing Sheet

MECHANICAL CLOSURE WITH SLIT CARRIER FOR DISPOSABLE DIAPERS

This application claims the priority of U.S. Provisional application Ser. No. 60/010,075, filed Jan. 16, 1996.

BACKGROUND OF THE INVENTION AND RELATED ART

The present invention relates to closures for fastening adjacent portions or edges of materials together. The closures are useful as fastening system closures for disposable diapers.

Diapers of this general type are widely used. A typical diaper construction comprises an absorbent pad or batt or the like enclosed in an outer plastic shell or a non-woven backsheet that is non-woven fabric laminated with a water impermeable layer such as a polyethylene film. A water permeable inner shell or liner is also provided to promote separation of fluid from the user.

The fastener tape system generally includes adhesive tabs fastened to one end of the diaper assembly construction at each lateral side of the diaper in a permanent "factory joint" by the diaper manufacturer using adhesives or other techniques. Heretofore, the tabs typically have a face coated with pressure-sensitive adhesive. The tabs are releasably attachable to the other end of the diaper at each lateral side in a "user joint". The attachment is releasable both to allow permanent removal of the diaper and to allow unfastening to inspect the diaper followed by refastening if indicated.

There is a need for a diaper tab having a user joint with a mechanical closure, and more particularly, an extensible or stretchable tab having such a mechanical closure. Such closures may include Velcro brand closures with mechanical engaging elements. The tab may engage a specially constructed mechanical receiving or engaging location at a landing member or the non-woven backsheet of a disposable diaper. Such mechanical closure members are typically nonextensible since the integral substrate and engaging elements are formed of relatively stiff and nonextensible materials or plastics. These nonextensible materials are used to assure that the engaging elements provide adequate strength and do not merely bend or flex with disengagement loads.

The use of combined adhesive and mechanical fastener systems is shown in U.S. Pat. Nos. 5,019,065, 5,053,028 and 4,869,724. The teachings of all of these patents being incorporated herein by reference.

Related art includes U.S. Pat. Nos. 4,795,456 and 4,834,820.

SUMMARY OF THE INVENTION

The present invention provides an extensible tab fastener system having a user joint that enables mechanical attachment. An extensible facestock cooperates with an ordinarily nonextensible mechanical fastener to form the extensible tab fastener in accordance with the present invention. The nonextensible mechanical fastener is rendered extensible by providing in at least the nonextensible portions thereof a plurality of separation interfaces or parting planes extending through the thickness of the nonextensible portion or portions at spaced locations in the direction of desired extensibility. The tab fastener system may be produced by high speed manufacturing processes.

DETAILED DESCRIPTION OF THE INVENTION

Figure 1:
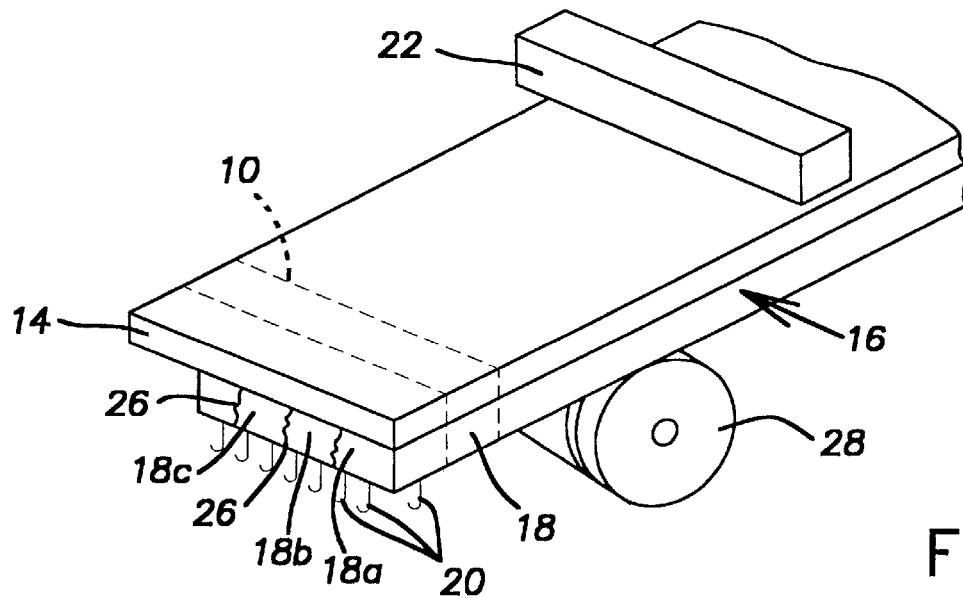
FIG. 1 is a schematic view showing apparatus for making stock for conversion to a diaper tab in accordance with the present invention.

Referring to FIG. 1, the production of stock for a diaper tab 10 is schematically shown in a single width size for convenience of illustration. As indicated in dotted outline, the diaper tab 10 is formed by cutting the stock across its width in the cross direction.

Figure 2:
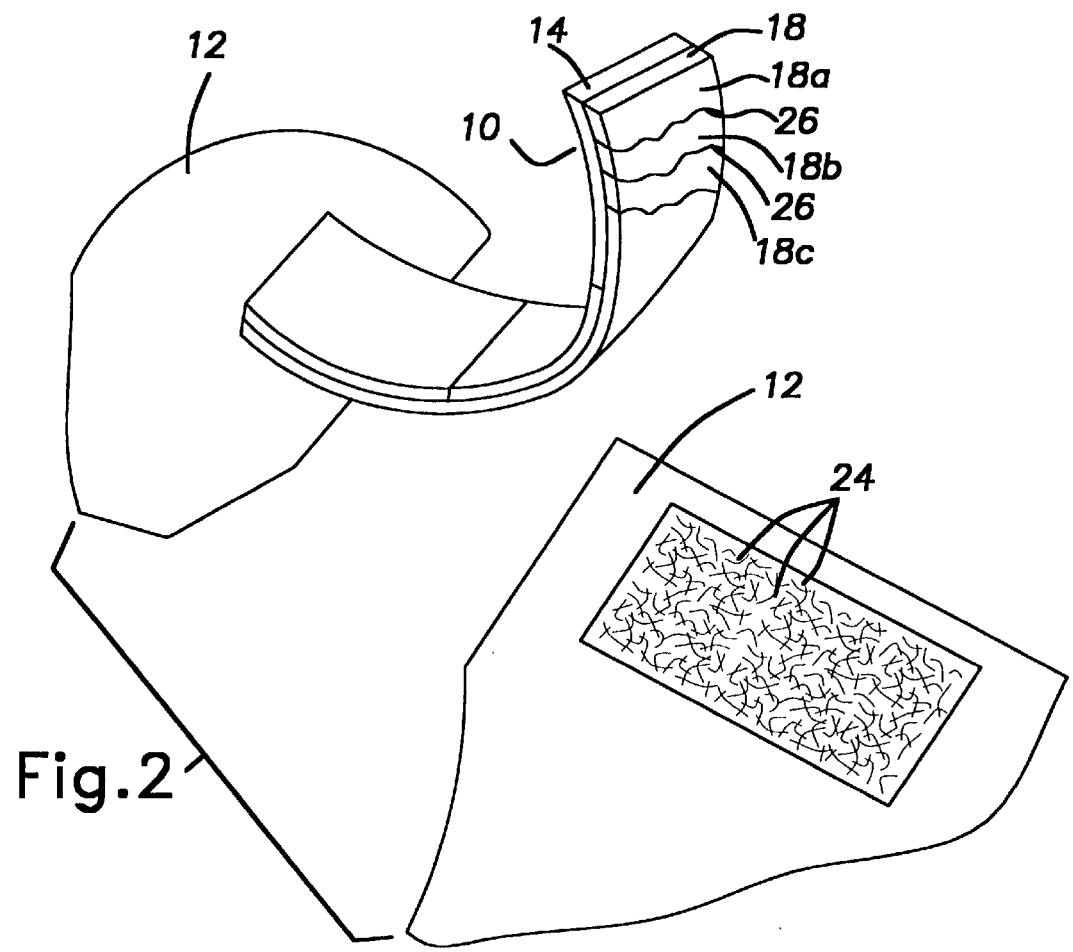
FIG. 2 is a perspective view showing a tab fastener applied to a diaper with the tab in the deployed position ready for closure.

Referring to FIG. 2, the diaper tab 10 is shown deployed for closure of a diaper 12. The diaper tab 10 includes a facestock film 14, a mechanical engagement or closure member 16 having a substrate 18 and protuberances or projecting elements 20 extending therefrom.

The facestock film 14 is extensible or stretchable. It may be separately formed by any suitable process and subsequently joined with the other layer portions of the tab 10, or it may be directly extruded onto the substrate 18 of the member 16. The facestock film 14 may be formed of elastomers such as the thermoplastic elastomers sold by the Shell Chemical Company under the designations Kraton. These elastomers may be SBS, SIS, SI, $S(IS)_X$ and SEBS block copolymers and mixtures thereof. The facestock may also comprise a polyurethane polymer of suitable elastic characteristics. Also, the facestock may be a stretchable non-woven fabric.

The facestock film 14 is joined to the member 16 by sonic welding, a hot melt adhesive or any other convenient manner to provide a permanent bond. In FIG. 1, a sonic welder 22 is shown in the production line for joining the facestock film 14 to the member 16. Alternatively, a pressure-sensitive adhesive may be used, such as an acrylic or a rubber pressure-sensitive adhesive as are well known in the art. Typical pressure-sensitive adhesives include acrylic resin and natural or synthetic based rubber adhesives. Preferred adhesives include hot melt pressure-sensitive adhesives of the A-B-A block copolymer type as disclosed in U.S. Pat. No. 3,932,328. Illustrative rubber based adhesives include styrene-isoprene-styrene and styrene-butadiene-styrene which may optionally contain diblock components. The adhesive may be applied using hot-melt, solvent or emulsion techniques.

The mechanical engagement member 16 comprises any of the well known hook and loop type engagement materials as particularly exemplified by the Velcro fabric materials sold by Velcro USA. The member 16 includes a substrate 18 and projecting elements or hooks 20. The member 16 is typically not extensible and, more particularly, the substrate 18 is not extensible since the elements 20 are discrete projections extending from the substrate. The elements 20 together with the member 16 may be formed of polypropylene, nylon, polyester or other relatively rigid polymer.

The mechanical elements 20 are integrally formed with the substrate 18 in the illustrated embodiment. The elements 20 extend generally perpendicular from the substrate 18. The elements 20 should be of sufficient length to provide mechanical engagement with a locking or engaging array of mechanical elements, or with a fibrous material such as a non-woven landing tape or member 24 as shown in FIG. 2 or a non-woven backsheet of a diaper.

Further, the polymer forming the member 16 should be of sufficient stiffness or rigidity to provide the elements 20 with the required shear strength engagement properties.

In accordance with the invention, the member 16 and more particularly the substrate 18 thereof is made extensible by a providing a plurality of separation interfaces or slits 26 which form parting planes extending through the thickness of the substrate at spaced locations along the length of the tab 10. The slits 26 may be formed with accurate dimensions assuring full cutting through the thickness of the substrate 18 by rotary die cutting as in the case of label preparation as is known in the art. A rotary die cutter 28 is shown in FIG. 1 for engagement with the substrate 18 through the elements 20. Such rotary die cutting is a high speed process that lends itself to economic production.

The slits 26 are spaced apart a decreasing distance with decreasing size of the elements 20. In typical diaper tab applications, the slits 26 may be spaced apart a distance of from about 0.1 to 0.5 inches as measured along the length of the tab 10 in the direction extensibility. This spacing may be even less for elements 20 of substantially small dimension.

The slits 26 effectively divide the substrate 18 into parallel segments 18a, 18b, 18c, etc., supported by the facestock film 14 The segments 18a, 18b, 18c, etc. and associated elements 20 are separable along the length of the tab 10 as shown in FIG. 2. This enables groups of elements 20 to separate from other groups of elements 20 as the facestock 14 and tab 10 is stretched. The tab 10 is thereby provided with an extensibility substantially corresponding with that of the facestock film 14.

For purposes of mounting the tab 10 to the diaper 12 at the factory joint, the member 16 has a width slightly less than that of the facestock film 14. The exposed proximal end (or left end in FIGS. 1 and 2) of the tab 10 may then be secured to the diaper 12 in any convenient manner by the diaper manufacturer, e.g. adhesive or sonic welding or other means.

It should be appreciated that the tab 10 in accordance with the invention may be adhesive free in respect to both the diaper closure engagement per se and the fastener construction.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A disposable diaper having opposed first and second ends and a fastening system for releasably securing said diaper ends together about a user, said fastening system including tab members secured to said first end of said diaper and a landing member secured to said second end of said diaper, said tab members and landing member being adapted to mechanically engage and disengage for diaper closure and opening, each of said tab members having a length along which they respectively engage said landing member, each said tab member including an extensible facestock superposed on and secured to a mechanical fastener, said mechanical fastener being coextensive with at least a portion of said tab member, said mechanical fastener including an ordinarily nonextensible substrate having opposed substrate faces, one of said substrate faces being secured to said facestock and the other of said substrate faces having discrete engagement members projecting therefrom, said substrate having in at least a portion thereof a plurality of separation interfaces extending through the thickness of the substrate at spaced locations in the direction of the length of said tab, said interfaces separating upon application of tension loads in the direction of the length of said tab to thereby render said substrate extensible.

2. A diaper as in claim 1, wherein said mechanical fastener comprises a hook and loop fastener.

3. A diaper as in claim 2, wherein said facestock comprises an elastomer or a stretchable non-woven fabric.

4. A diaper as in claim 3, wherein said separation interfaces are provided by slits.

5. A diaper as in claim 3, wherein said separation interfaces are spaced apart a distance of from about 0.1 to 0.5 inches as measured along the length of said tab.

6. A diaper as in claim 5, wherein said tab member has a proximal end secured to said diaper and said mechanical fastener overlies a portion of said tab member remote of said proximal end of said tab member.

7. A diaper as in claim 1, wherein said mechanical fastener substrate and engagement members are integrally formed.

8. A diaper as in claim 1, wherein said mechanical fastener substrate and engagement members are formed of a single polymer.

9. A diaper as in claim 1, wherein said mechanical fastener is a VELCRO® brand closure with mechnical engaging elements.

* * * * *